(12) United States Patent
Takahira

(10) Patent No.: US 10,959,603 B2
(45) Date of Patent: Mar. 30, 2021

(54) PROCESSOR DEVICE FOR ENDOSCOPE AND ENDOSCOPE DATA COLLECTION SERVER

(71) Applicant: FUJIFILM Corporation, Tokyo (JP)

(72) Inventor: Masayuki Takahira, Kanagawa (JP)

(73) Assignee: FUJIFILM Corporation, Tokyo (JP)

( * ) Notice: Subject to any disclaimer, the term of this patent is extended or adjusted under 35 U.S.C. 154(b) by 79 days.

(21) Appl. No.: 16/387,492

(22) Filed: Apr. 17, 2019

(65) Prior Publication Data
US 2019/0320880 A1  Oct. 24, 2019

(30) Foreign Application Priority Data

Apr. 18, 2018 (JP) .............................. JP2018-079877

(51) Int. Cl.
| | |
|---|---|
| G06F 15/16 | (2006.01) |
| A61B 1/00 | (2006.01) |
| G16H 40/40 | (2018.01) |
| G06F 11/07 | (2006.01) |

(52) U.S. Cl.
CPC ........ *A61B 1/00057* (2013.01); *A61B 1/0002* (2013.01); *A61B 1/00011* (2013.01); *A61B 1/00055* (2013.01); *G06F 11/0751* (2013.01); *G16H 40/40* (2018.01); *A61B 1/00006* (2013.01); *A61B 2560/0271* (2013.01)

(58) Field of Classification Search
CPC ............ A61B 1/00057; A61B 1/00011; A61B 1/0002; A61B 1/00055; A61B 1/00006; A61B 2560/0271; G16H 40/40; G06F 11/0751

USPC ........................................................ 709/236
See application file for complete search history.

(56) References Cited

U.S. PATENT DOCUMENTS

| | | | |
|---|---|---|---|
| 10,601,639 B2 * | 3/2020 | Ratakonda | H04L 43/0823 |
| 2002/0126204 A1 * | 9/2002 | Takeshige | H04N 7/18 348/74 |
| 2005/0196314 A1 * | 9/2005 | Petersen | A61B 1/12 422/3 |
| 2006/0106284 A1 * | 5/2006 | Shouji | G16H 10/60 600/118 |
| 2009/0150537 A1 * | 6/2009 | Fanson | H04L 41/0896 709/224 |
| 2013/0288735 A1 * | 10/2013 | Guo | H04W 4/08 455/509 |
| 2016/0210419 A1 * | 7/2016 | Kuji | G16H 40/40 |

(Continued)

FOREIGN PATENT DOCUMENTS

| | | |
|---|---|---|
| JP | 2002263063 | 9/2002 |
| JP | 2014008126 | 1/2014 |

OTHER PUBLICATIONS

Translation of JP2014-008126 A, translated by JPO (Year: 2014).*

(Continued)

*Primary Examiner* — Imad Hussain
(74) *Attorney, Agent, or Firm* — JCIPRNET

(57) ABSTRACT

An endoscope data transmission unit transmits first endoscope-running data to an endoscope data collection server through a specific network at a first timing. The endoscope data transmission unit transmits second endoscope-running data, of which the volume is larger than the volume of the first endoscope-running data, to the endoscope data collection server at a second timing including a timing when an error is generated.

10 Claims, 5 Drawing Sheets

(56) References Cited

U.S. PATENT DOCUMENTS

2017/0135558 A1* 5/2017 Choi .................. A61B 1/015
2017/0207948 A1* 7/2017 Ratakonda .......... H04L 41/0631
2019/0116332 A1* 4/2019 Adachi ............... H04N 5/3765
2019/0306070 A1* 10/2019 Zheng ................. H04L 1/0002

OTHER PUBLICATIONS

Translation of JP2014-008126 A, translated by Google (Year: 2014).*
"Search Report of Europe Counterpart Application", dated Sep. 23, 2019, pp. 1-9.

* cited by examiner

| ENDOSCOPE INFORMATION | | | | | |
|---|---|---|---|---|---|
| A: IMAGING-UNIT INFORMATION | | B: SCOPE-OPERATION-UNIT INFORMATION | | C: SCOPE-CONTROL-UNIT INFORMATION | |
| 1 | TEMPERATURE | 1 | SWITCH (SW) OPERATION | 1 | VOLTAGE |
| 2 | HUMIDITY | 2 | ANGLE OPERATION | 2 | COMMUNICATION LOGS |
| 3 | PRESSURE | | | 3 | VIDEO COMMUNICATION SITUATION |
| 4 | OUTPUT VIDEO | | | | |
| 5 | LIGHT QUANTITY DATA | | | | |

FIG. 5

| D: LIGHT-SOURCE INFORMATION | | E: PROCESSOR INFORMATION | |
|---|---|---|---|
| 1 | LIGHT-SOURCE-OPERATION-UNIT INFORMATION | 1 | PROCESSOR-OPERATION-UNIT INFORMATION |
| 2 | LIGHT-SOURCE-CONTROL-UNIT INFORMATION | 2 | ENDOSCOPY-DATA-COMMUNICATION SITUATION |
| | | 3 | ENDOSCOPY-IMAGE-COMMUNICATION SITUATION |
| | | 4 | DEVICE-SETTING INFORMATION |

| FIRST TRANSMISSION-INFORMATION SETTING TABLE | |
|---|---|
| ERROR NUMBER | OUTPUT INFORMATION |
| E0001 | B1,B2 |
| E0002 | A1 TO A3,B1,B2 |

| SECOND TRANSMISSION-INFORMATION SETTING TABLE | | |
|---|---|---|
| ERROR NUMBER | COMMUNICATION SITUATION | OUTPUT INFORMATION |
| E0001 | SLOW | B1,B2 |
| E0002 | FAST | B1,B2,C1 TO C3 | ns
PROCESSOR DEVICE FOR ENDOSCOPE AND ENDOSCOPE DATA COLLECTION SERVER

CROSS-REFERENCE TO RELATED APPLICATIONS

This application claims priority under 35 U.S.C § 119(a) to Japanese Patent Application No. 2018-079877 filed on 18 Apr. 2018. The above application is hereby expressly incorporated by reference, in its entirety, into the present application.

BACKGROUND OF THE INVENTION

1. Field of the Invention

The present invention relates to a processor device for an endoscope, which transmits endoscope-running data, such as operation information of an endoscope, to an external server, and an endoscope data collection server.

2. Description of the Related Art

Endoscopic diagnosis, which uses an endoscope system comprising an endoscope, a light source device, and a processor device, is performed in a medical field. For example, in a case where a light source lamp, which easily deteriorates with age, such as a xenon lamp, is used in the light source device of the endoscope system, the light source lamp needs to be replaced regularly. However, since the time when maintenance is to be performed or the time when the light source lamp is to be replaced varies for each endoscope system, there are many cases where a timing when maintenance is to be performed cannot be known.

In contrast, in JP2002-263063A (corresponding to US2002/126204A1), a processor device for an endoscope includes a monitoring circuit for monitoring devices connected to a processor for an endoscope and is adapted to inform an endoscope data collection server, which is connected to a network, of monitoring results of the monitoring circuit. Accordingly, the time when maintenance is to be performed and the like can be grasped in the endoscope data collection server.

SUMMARY OF THE INVENTION

In a case where endoscope-running data, such as monitoring results, is transmitted to an external endoscope data collection server from the processor device for an endoscope as disclosed in JP2002-263063A, generally, the speed of communication between an external network and the processor device for an endoscope is not so much high. Further, since there is a possibility that power may be shut off after endoscopy using an endoscope system ends, a timing when the endoscope-running data is to be transmitted may be missed in a certain situation. For this reason, it is necessary to send endoscope-running data to a server provided in a hospital once and to send the endoscope-running data to an external server from the server according to a situation.

There is a case where an image retention server retaining endoscopic images may be used as a server that temporarily retains endoscope-running data in the server provided in the hospital. However, there is a case where the image retention server cannot be used if the matching between a server manufactured by a popular manufacturer or the like and the image retention server is poor. Accordingly, in a case where endoscope-running data should be retained in the hospital, there are many cases where new equipment needs to be prepared. For this reason, there are problems that costs are increased, the installation site of the equipment should be ensured, and the maintenance of the equipment should be performed, and the like. Further, since there are not too many cases where communication infrastructure provided in the hospital cannot be used as it is from the viewpoint of security, there is a problem that costs, such as communication costs, are increased in a case where a device, such as a virtual private network (VPN), or a separate network is to be constructed as a network used for the communication of endoscope-running data.

In regard to the above-mentioned problems, even though a communication line of which the speed of communication is low is used, endoscope-running data needs to be capable of being transmitted to the endoscope data collection server as soon as the endoscope-running data is generated, and endoscope-running data required for the analysis of the cause of an error, a trouble, or the like needs to be capable of reliably being transmitted to the endoscope data collection server.

An object of the invention is to provide a processor device for an endoscope, which can transmit endoscope-running data required for the analysis of the causes of an error and the like while reducing costs required for the communication of endoscope-running data, such as network-related equipment and communication costs, and an endoscope data collection server.

The invention provides a processor device for an endoscope connectable to a specific network. The processor device for an endoscope comprises an endoscope data transmission unit that transmits first endoscope-running data to an endoscope data collection server through the specific network at a first timing and transmits second endoscope-running data of which a volume is larger than a volume of the first endoscope-running data at a second timing including a timing when an error is generated.

It is preferable that the second endoscope-running data is device-related information related to operation information, working information, or processing information of an endoscope, a light source device, or a processor body. It is preferable that the processor device for an endoscope further comprises a first transmission-information setting table in which the error and the device-related information are associated with each other and the endoscope data transmission unit transmits the device-related information associated with the generated error as the second endoscope-running data with reference to the first transmission-information setting table in a case where the error is generated.

It is preferable that the processor device for an endoscope further comprises a second transmission-information setting table in which the error, the device-related information, and a transmission volume level regarding a volume of the second endoscope-running data to be transmitted are associated with one another and the endoscope data transmission unit transmits the device-related information, which is associated with the error and the transmission volume level, as the second endoscope-running data with reference to the second transmission-information setting table in a case where the error is generated. The transmission volume level is determined according to a communication situation of the specific network. It is preferable that the volume of the device-related information to be transmitted is increased as a transmission speed of the specific network is higher. It is preferable that the transmission volume level is determined by a user's setting. The processor device for an endoscope further comprises a transmission volume level-changing unit that changes a transmission volume level regarding a volume of the second endoscope-running data to be transmitted, and the endoscope data transmission unit transmits the second endoscope-running data that is based on a transmission volume level changed by the transmission volume level-changing unit.

It is preferable that the first endoscope-running data includes at least identification information of the endoscope, identification information of the light source device, or identification information of the processor body. It is preferable that the first timing and the second timing are the same timing or different timings.

The invention provides an endoscope data collection server connected to a processor device for an endoscope through a specific network. The endoscope data collection server comprises an endoscope data reception unit that receives first endoscope-running data transmitted from the processor device for an endoscope through the specific network at a first timing and receives second endoscope-running data, which is transmitted from the processor device for an endoscope and of which a volume is larger than a volume of the first endoscope-running data, through the specific network at a second timing including a timing when an error is generated.

According to the invention, it is possible to transmit endoscope-running data required for the analysis of the causes of an error and the like while reducing costs required for the communication of endoscope-running data, such as network-related equipment and communication costs.

BRIEF DESCRIPTION OF THE DRAWINGS

FIG. 5 is a table showing light-source information and processor information.

FIG. 6 is a table showing a first transmission-information setting table.

FIG. 7 is a table showing a second transmission-information setting table.

DESCRIPTION OF THE PREFERRED EMBODIMENTS

Figure 1:
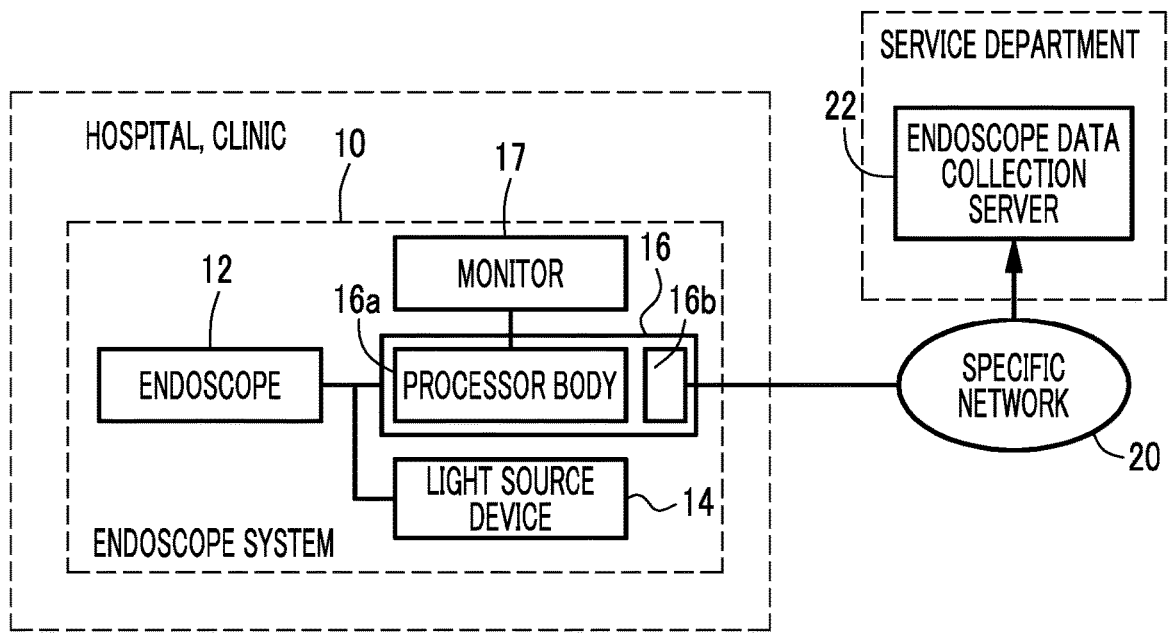
FIG. 1 is a conceptual diagram showing an endoscope system that is provided in a hospital or a clinic and an endoscope data collection server that is connected to the endoscope system through a specific network.

As shown in FIG. 1, an endoscope system 10 is provided for endoscopy in medical facilities, such as a hospital and a clinic. The endoscope system 10 comprises an endoscope 12 that is to be inserted into the body of a patient, a light source device 14 that supplies illumination light for illuminating the inside of the body of the patient to the endoscope 12, and a processor device 16 (a processor device for an endoscope) that performs image processing on the image of an object to be observed taken by the endoscope 12. Further, a monitor 17, which is used to display images and the like output from the processor device 16, is connected to the processor device 16.

The processor device 16 can be connected to a specific network 20, and can communicate with an endoscope data collection server 22, which is used to collect endoscope-running data, through the specific network 20. It is preferable that the endoscope data collection server 22 is installed in a service department for performing the maintenance of the endoscope 12 or the like, and the usage and the like of an endoscope are analyzed using the endoscope-running data in the service department. As described later, the endoscope-running data includes: first endoscope-running data that includes the identification information of at least the endoscope 12, the light source device 14, or a processor body 16a; and second endoscope-running data that includes device-related information related to the operation information, the working information, or the processing information of the endoscope 12, the light source device 14, or the processor body 16a.

Since a mobile phone network, which is a closed network, is used in this embodiment as the specific network 20, a connection device 16b (for example, 3G/LTE communication modem), which is used to be connected to a mobile phone network, is built in the processor device 16 in addition to the processor body 16a performing image processing and the like. For example, a virtual private network (VPN) constructed on the Internet may be used as the specific network.

Figure 2:
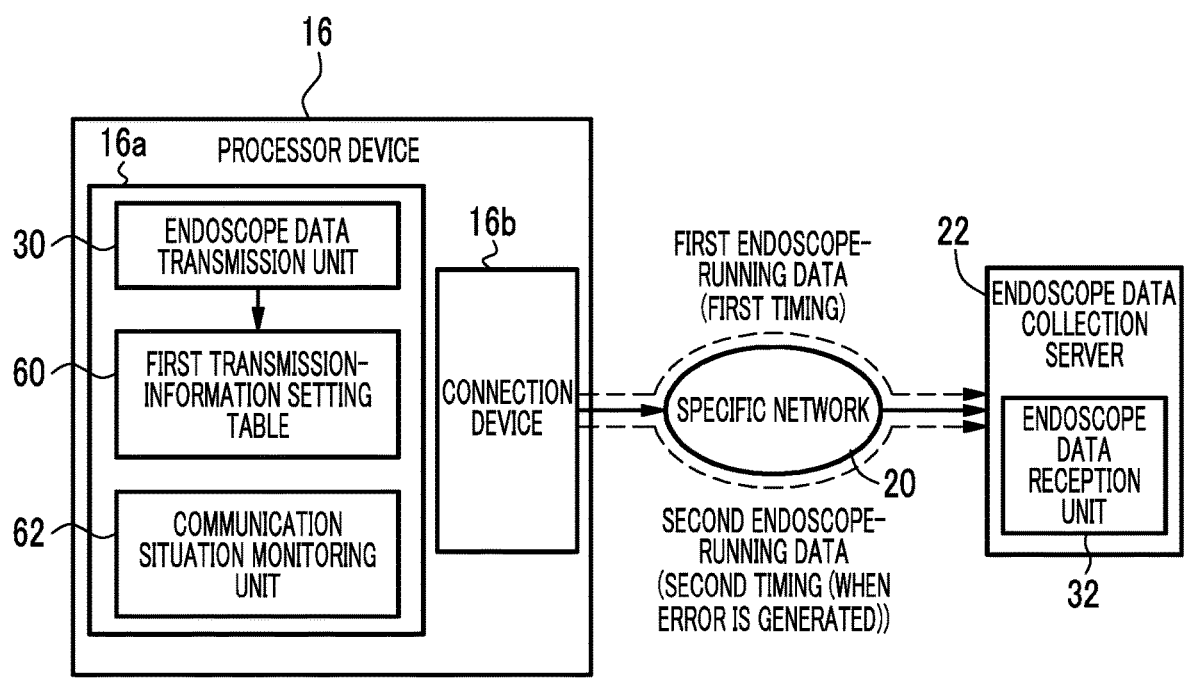
FIG. 2 is a diagram illustrating data that is transmitted to the endoscope data collection server from a processor device.

As shown in FIG. 2, the processor body 16a of the processor device 16 comprises an endoscope data transmission unit 30 that transmits the first endoscope-running data at a first timing and transmits the second endoscope-running data at a second timing different from the first timing and including a timing when an error is generated. The error is to notify the fact that at least one of the endoscope 12, the light source device 14, or the processor body 16a included in the endoscope system 10 does not operate normally, the fact that an abnormal image difficult to be used for endoscopy is displayed, or the like, by using voice or a display on the monitor 17.

A plurality of errors are present and include, for example, a temperature abnormality, a humidity abnormality, an air-tightness abnormality, a voltage abnormality, a video abnormality, an initialization abnormality, a communication abnormality, an image-transmission abnormality, a printing abnormality, a light-quantity abnormality, a light-source-life warning, a parameter-switching abnormality, an angle operation abnormality, and the like. Among these errors, the temperature abnormality, the humidity abnormality, and the airtightness abnormality include abnormalities of temperature, humidity, and airtightness at the distal end portion of the endoscope. The voltage abnormality means that voltages of the endoscope 12, the light source device 14, and the processor body 16a are out of the range of a normal voltage value. The video abnormality means that an abnormality is generated in an image displayed on the monitor 17. The initialization abnormality means that initialization processing for returning the endoscope system 10 to a state obtained at the time of shipment is not performed normally. The communication abnormality means that an abnormality is generated in the communication between the endoscope 12 and the processor body 16a and the communication between the light source device 14 and the processor body 16a.

Further, the image-transmission abnormality means that an abnormality is generated in transmission processing for sending an image to the processor body 16a from the endoscope 12. The printing abnormality means that an abnormality is generated in a printer connected to the processor body 16a. The light-quantity abnormality means that the quantity of light emitted from the light source device 14 is out of an allowable range. The light-source-life warning is warning used to inform that a light source built in the light source device 14 cannot emit light of which the quantity is adequate due to deterioration. Further, the parameter-switching abnormality means that an abnormality is generated in the switching of parameters of image processing performed in the processor body 16a during the switching of an observation mode. The angle operation abnormality means that an abnormality is generated in the angle operation of the distal end portion of the endoscope 12.

Furthermore, an error number (for example, "E0001", "E0002", and the like) is given to each of types of errors. The volume of the first endoscope-running data is made smaller than the volume of the second endoscope-running data. In the endoscope data collection server, an endoscope data reception unit 32 receives the first endoscope-running data at the first timing and receives the second endoscope-running data at the second timing.

The first timing and the second timing may be the same timing or different timings. For example, the first timing and the second timing are set to the same timing and both the first endoscope-running data and the second endoscope-running data are sent, so that a lot of information required for the analysis of the cause of an error can be collected. On the other hand, in a case where an error is generated, the first timing and the second timing may be made different from each other and only the second endoscope-running data may be transmitted to reduce the volume of data to be transmitted. Further, the first timing is set to a specific timing interval (for example, an interval of 2 sec.), so that the first endoscope-running data may continue to be transmitted at a specific timing interval during the endoscopy using endoscope system 10.

Here, the volume of the first endoscope-running data to be transmitted at the first timing except for the time of generation of an error is reduced so that the first endoscope-running data can be reliably transmitted to the endoscope data collection server 22 even in a case where a transmission speed of the specific network 20 is low. It is preferable that the first endoscope-running data is the minimum information required to specify the endoscope system 10. For example, it is preferable that the first endoscope-running data includes at least identification information, such as the types of devices and serial Nos., used to identify the endoscope 12, the light source device 14, and the processor body 16a. The first endoscope-running data may include endoscopy time. However, in a case where endoscopy time cannot be output from the processor device 16, it is preferable that the first endoscope-running data includes the power-on time and power-off time of the processor device 16 and the endoscopy time is calculated from the power-on time and the power-off time at the time when the endoscope data collection server collects data.

In contrast, since information required for the analysis of the cause of an error and the like needs to be transmitted in addition to or instead of information used to specify the endoscope system 10 as the second endoscope-running data to be transmitted at the second timing including a timing when an error is generated, the volume of the second endoscope-running data is made larger than the volume of the first endoscope-running data. Here, it is preferable that the second endoscope-running data includes device-related information related to the working or processing of the endoscope 12, the light source device 14, or the processor body 16a. Further, the second endoscope-running data may include an abnormal image that is obtained at the time of generation of an error.

Figures 3, 4:
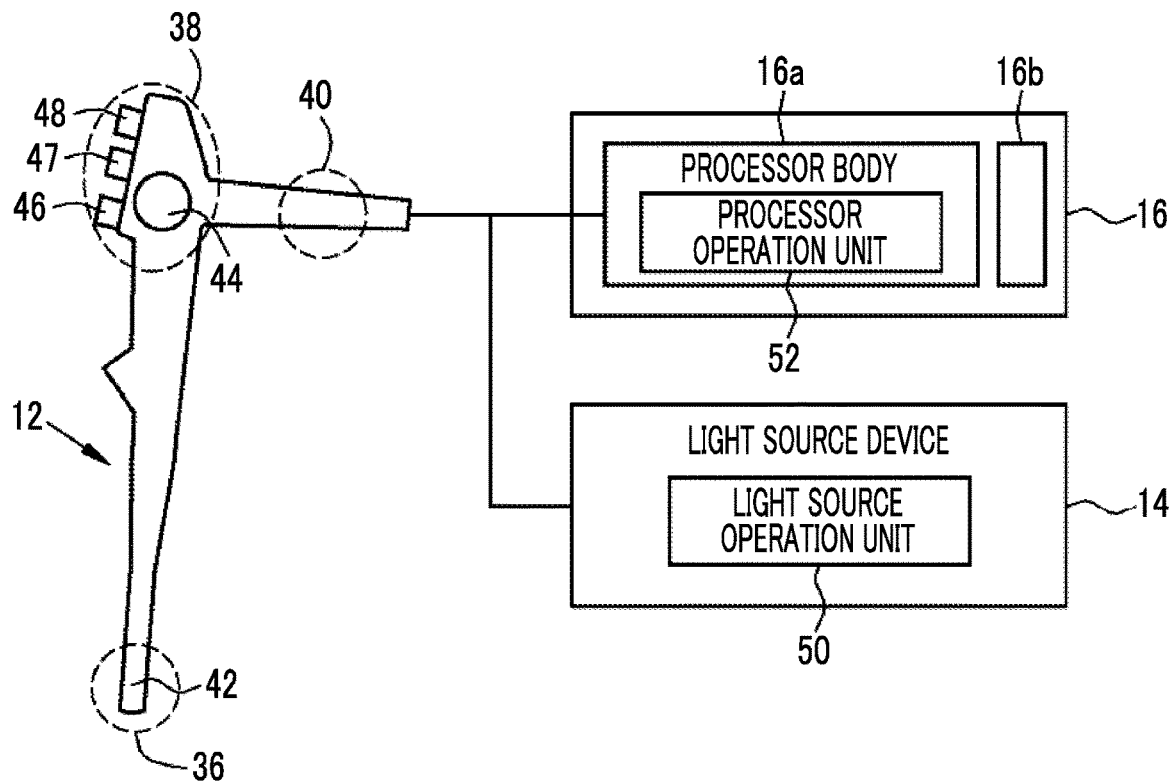
FIG. 3 is a conceptual diagram showing an endoscope, a processor device, and a light source device.
FIG. 4 is a table showing endoscope information.

As shown in FIG. 3, A: imaging-unit information about an imaging unit 36 of the endoscope 12, B: scope-operation-unit information about an operation unit 38 of the endoscope 12, or C: scope-control-unit information about a control unit 40 of the endoscope 12 is included as the device-related information of the endoscope 12. As shown in FIG. 4, temperature ("temperature" in FIG. 4), humidity ("humidity" in FIG. 4), or pressure ("pressure" in FIG. 4) of a distal end portion 42 of the endoscope 12 is included as A: imaging-unit information. It is preferable that sensors are provided at the distal end portion 42 of the endoscope 12 to measure the temperature, the humidity, and the pressure. In addition, video signals ("output video" in FIG. 4), which are output from an imaging sensor (not shown), and light quantity data ("light quantity data" in FIG. 4), which represents the brightness information of an object to be observed obtained from the video signals, are included as A: imaging-unit information. Numbers are given to device-related information of A: imaging-unit information so that 1 denotes "temperature", 2 denotes "humidity", 3 denotes "pressure", 4 denotes "output video", and 5 denotes "light quantity data". Likewise, numbers are also given to device-related information of B: scope-operation-unit information, C: scope-control-unit information, D: light-source information, and E: processor information to be described below.

Switch operation information ("switch (SW) operation" in FIG. 4) about the operation of various switches SW provided on the operation unit 38 of the endoscope 12 or angle operation information ("angle operation" in FIG. 4) about the operation of an angle knob 44 used to change the orientation of the distal end portion 42 of an insertion part is included as B: scope-operation-unit information. A voltage ("voltage" in FIG. 4) of a processing circuit of the endoscope 12, communication logs ("communication logs" in FIG. 4) between the endoscope 12 and the processor body 16a, or a video communication situation ("video communication situation" in FIG. 4) regarding video signals is included as C: scope-control-unit information. It is preferable that the operation unit of the endoscope 12 is provided with, for example, a freeze button 46 used to acquire the static image of an object to be observed, a mode changeover SW 47 used to switch the pattern of illumination light or an image display pattern, and a zoom operation part 48 used to increase or reduce the size of the displayed image of the object to be observed.

As shown in FIGS. 3 and 5, D: light-source information about the light source device 14 is included as the device-related information of the light source device 14. Light-source-operation-unit information ("light-source-operation-unit information" in FIG. 5) about the operation of a light source operation unit 50, such as a power switch for the light source or a light quantity-adjustment button, or information ("light-source-control-unit information" in FIG. 5) about the control of the light source built in the light source device, such as control associated with a light quantity-adjustment operation or an operation for switching the light source according to an observation mode, is included as D: light-source information.

As shown in FIGS. 3 and 5, E: processor information about the processor body 16a is included as device-related information of the processor body 16a. Processor-operation-unit information ("processor-operation-unit information" in FIG. 5) about the operation of a processor operation unit 52, such as an operation for switching an observation mode, a communication situation ("endoscopy-data-communication situation" in FIG. 5) of endoscopy data (a patient name, sex, an endoscopy date, and the like) to be transmitted to an endoscope management system (not shown) provided in a hospital, a communication situation ("endoscopy-image-communication situation" in FIG. 5) of an endoscopy image to be transmitted to an endoscopic image management system (not shown) provided in the hospital, or various pieces of device-setting information ("device-setting information" in FIG. 5) for the endoscope 12, the light source device 14, and processor body 16a (for example, a switch of the operation unit of the endoscope 12 to which a function of "static image-retaining instruction" is assigned, and the like) is included as E: processor information.

In a case where the endoscope data transmission unit 30 transmits the second endoscope-running data at the second timing, the endoscope data transmission unit 30 transmits the second endoscope-running data with reference to a first transmission-information setting table 60. As shown in FIG. 6, the cause of an error and device-related information having a correlation with the cause of an error are stored in the first transmission-information setting table 60 in association with each other as an error number that indicates an error and output information that is to be output when an error is generated. For example, information about "switch (SW) operation" of B1 and information about "angle operation" of B2 are associated with an error number as the device-related information corresponding to error number "E0001". Accordingly, information about "switch (SW) operation" of B1 and information about "angle operation" of B2 are transmitted to the endoscope data collection server at a timing when an error having error number "E0001" is generated.

Further, "temperature" of A1, "humidity" of A2, "pressure" of A3, "switch (SW) operation" of B1, and "angle operation" of B2 are stored in the first transmission-information setting table 60 in association with an error number as the device-related information corresponding to error number "E0002". Accordingly, information about "temperature" of A1, information about "humidity" of A2, information about "pressure" of A3, information about "switch (SW) operation" of B1, and information about "angle operation" of B2 are transmitted to the endoscope data collection server at a timing when an error having error number "E0002" (of which the contents are different from the contents of the error having error number "E0001") is generated. In a case where the contents of the errors are different from each other as described above, devices, which are likely to cause the errors to be generated, are also different from each other. For this reason, device-related information associated with an error number indicating an error also varies for each error.

The processor device 16 is adapted to be capable of changing the volume of the second endoscope-running data, which is to be transmitted at the second timing, according to the communication situation of the specific network 20. In this case, a second transmission-information setting table 65 shown in FIG. 7 is used instead of the first transmission-information setting table 60. That is, in a (specific) case where the communication situation of the specific network 20 is fast (a transmission speed is equal to or higher than a specific threshold value), the volume of the second endoscope-running data to be transmitted is increased as a transmission volume level about the volume of data to be transmitted. On the other hand, in a case where the communication situation of the specific network 20 is slow (a transmission speed is lower than the specific threshold value), the volume of the second endoscope-running data to be transmitted is reduced as a transmission volume level. The communication situation of the specific network 20 is acquired by a communication situation monitoring unit 62 provided in the processor body 16a. The communication situation monitoring unit 62 measures the communication situation of the specific network 20 by transmitting/receiving test signals to/from the specific network 20.

In this embodiment, the second transmission-information setting table 65 is set so that a transmission volume level is determined according to the communication situation of the specific network 20. That is, not only an error and device-related information having a correlation with the cause of the error but also the communication situation of the specific network 20 is stored in the second transmission-information setting table 65 in association with one another. As shown in FIG. 7, only information about "switch (SW) operation" of B1 and information about "angle operation" of B2 are adapted to be transmitted as the device-related information corresponding to error number "E0001" so that the volume of data to be transmitted is reduced in a case where the communication situation of the specific network 20 is "slow". On the other hand, not only "switch (SW) operation" of B1 and "angle operation" of B2 but also "voltage" of C1, "communication logs" of C2, and "video communication situation" of C3 are adapted to be transmitted as the device-related information corresponding to error number "E0001" so that the volume of data to be transmitted can be increased in a case where the communication situation of the specific network 20 is "fast".

In the second transmission-information setting table 65, a transmission volume level is determined so as to correspond to the communication situation of the specific network 20. However, a transmission volume level may be adapted to be determined on the basis of another criterion. For example, a transmission volume level may be adapted to be determined by user's settings. In this case, a user operates a user interface (not shown) used to determine a transmission volume level, so that a transmission volume level is determined in the processor body 16a. Examples of a criterion, which is used to determine a transmission volume level by a user, include the communication costs of the specific network 20, and the like.

Figure 8:
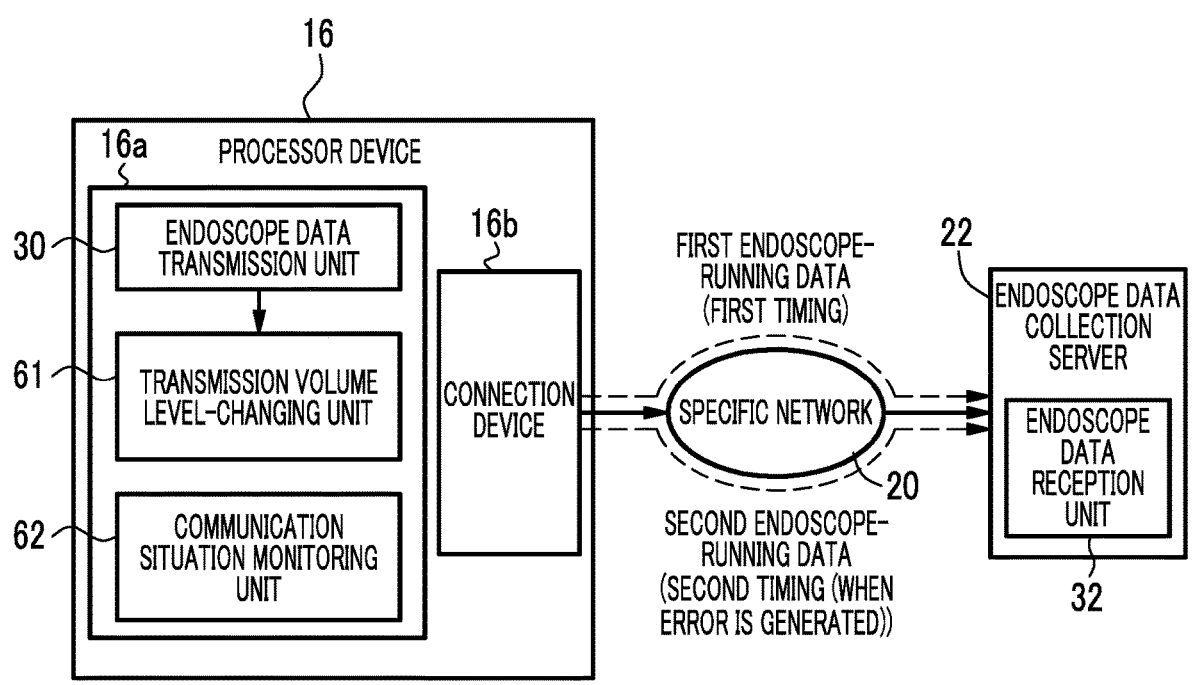
FIG. 8 is a diagram illustrating a processor device of which the transmission volume level can be changed.

Device-related information, which is determined in advance according to a transmission volume level, has been adapted to be transmitted in the embodiment, but the volume of the second endoscope-running data to be transmitted may be adapted to change in real time. In this case, a transmission volume level-changing unit 61, which changes the volume of the second endoscope-running data to be transmitted, is provided in the processor device 16 as shown in FIG. 8. The endoscope data transmission unit 30 is adapted to transmit the second endoscope-running data that is based on the volume of data to be transmitted changed by the transmission volume level-changing unit 61. It is preferable that the transmission volume level-changing unit 61 automatically changes a transmission volume level according to the communication situation of the specific network.

Figure 9:
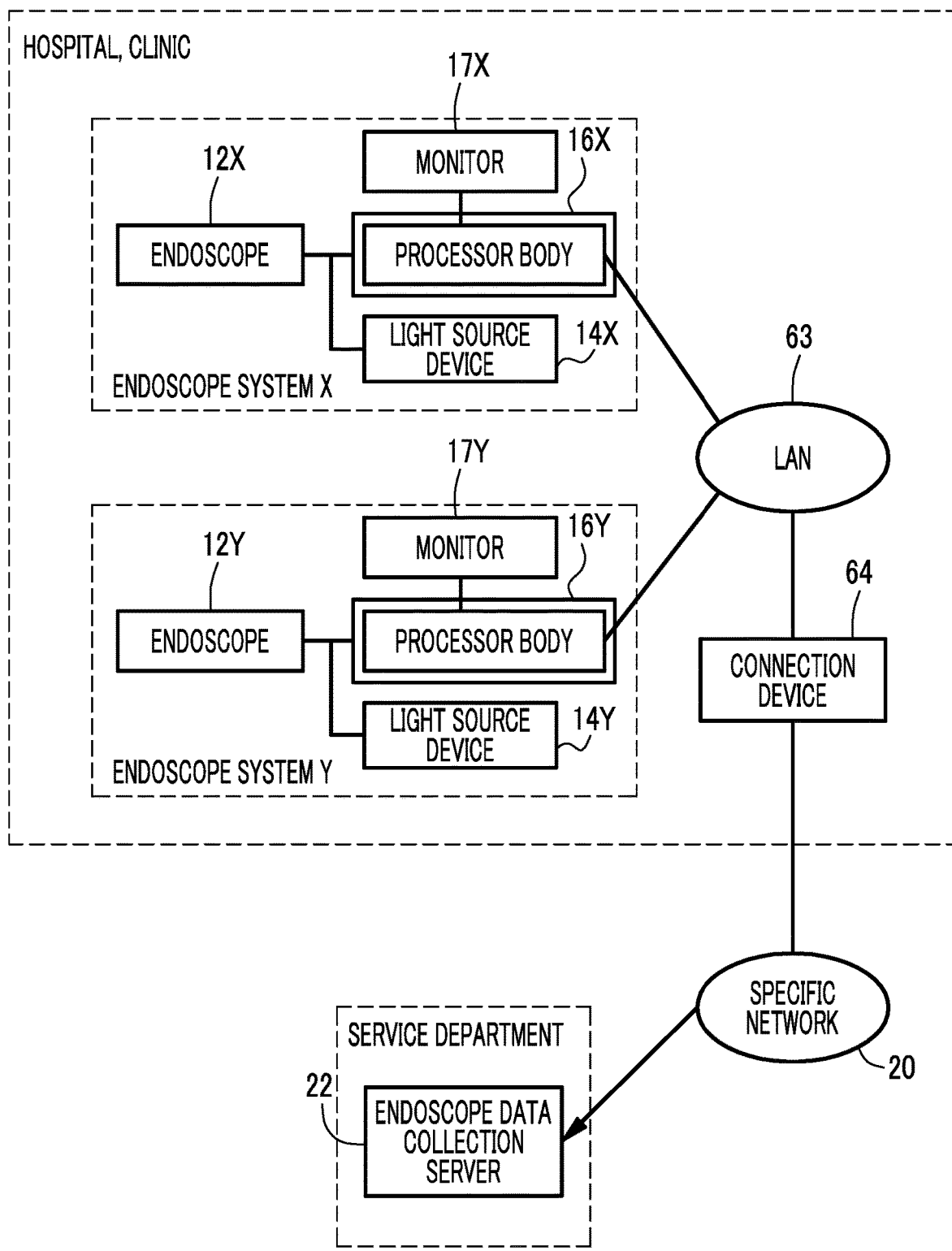
FIG. 9 is a conceptual diagram showing a plurality of endoscope systems that are provided in a hospital or a clinic and an endoscope data collection server that is connected to the endoscope systems through a specific network.

A case where one endoscope system is connected to the specific network 20 has been described in the embodiment, but a plurality of endoscope systems may be connected to the specific network 20. In this case, it is preferable that a plurality of endoscope systems, such as an endoscope system X comprising an endoscope 12X, a light source device 14X, a processor device 16X, and a monitor 17X and an endoscope system Y comprising an endoscope 12Y, a light source device 14Y, a processor device 16Y, and a monitor 17Y, are connected to a local area network (LAN) and a connection device 64 (for example, 3G/LTE router (gateway)), which is used to connect the LAN to the specific network 20, is installed as shown in FIG. 9.

In the embodiment, the hardware structures of processing units, which perform various kinds of processing, such as the endoscope data transmission unit 30, the endoscope data reception unit 32, and the communication situation monitoring unit 62, are various processors to be described later. Various processors include: a central processing unit (CPU) that is a general-purpose processor functioning as various processing units by executing software (program); a programmable logic device (PLD) that is a processor of which the circuit configuration can be changed after the manufacture of a field programmable gate array (FPGA) and the like; a dedicated electrical circuit that is a processor having circuit configuration designed for exclusive use to perform various kinds of processing; and the like.

One processing unit may be formed of one of these various processors, or may be formed of a combination of two or more same kind or different kinds of processors (for example, a plurality of FPGAs or a combination of a CPU and an FPGA). Further, a plurality of processing units may be formed of one processor. As an example where a plurality of processing units are formed of one processor, first, there is an aspect where one processor is formed of a combination of one or more CPUs and software so as to be typified by a computer, such as a client or a server, and functions as a plurality of processing units. Second, there is an aspect where a processor fulfilling the functions of the entire system, which includes a plurality of processing units, by one integrated circuit (IC) chip is used so as to be typified by System On Chip (SoC) or the like. In this way, various processing units are formed using one or more of the above-mentioned various processors as hardware structures.

In addition, the hardware structures of these various processors are more specifically electrical circuitry where circuit elements, such as semiconductor elements, are combined.

The invention has been applied to the processor device for an endoscope, but can also be applied to other medical devices. For example, the invention can be applied to In Vitro Diagnostics (IVD) that can be connected to the specific network 20. In this case, measurement results obtained from the in vitro diagnostics are transmitted to a measurement result collection server for constant connection through the specific network 20.

EXPLANATION OF REFERENCES

10: endoscope system
12: endoscope
12X: endoscope
12Y: endoscope
14: light source device
14X: light source device
14Y: light source device
16: processor device
16a: processor body
16b: connection device
16X: processor device
16Y: processor device
17: monitor
17X: monitor
17Y: monitor
20: specific network
22: endoscope data collection server
30: endoscope data transmission unit
32: endoscope data reception unit
36: imaging unit
38: operation unit
40: control unit
42: distal end portion
44: angle knob
46: freeze button
48: zoom operation part
50: light source operation unit
52: processor operation unit
60: first transmission-information setting table
61: transmission volume level-changing unit
62: communication situation monitoring unit
63: local area network (LAN)
64: connection device
65: second transmission-information setting table

What is claimed is:

1. A processor device for an endoscope connectable to a specific network, the device comprising:
a processor, configured to:
obtain a monitored result of at least one of the endoscope, a light source device, or a processor body in an endoscope system;
transmit first endoscope-running data to an endoscope data collection server through the specific network at a first timing; and
transmit second endoscope-running data of which a volume is larger than a volume of the first endoscope-running data to the endoscope data collection server at a second timing, a timing when an error is generated, to notify that at least one of the endoscope, the light source device, or the processor body in the endoscope system is not operating normally according to the monitored result of the at least one of the endoscope, the light source device, or the processor body, wherein
the error comprises an abnormality indicating the monitored result of at least one of the endoscope, the light source device, or the processor body is out of range, and
the second endoscope-running data is device-related information related to operation information, working information, or processing information of the endoscope, the light source device, or the processor body.

2. The processor device for an endoscope according to claim 1, further comprising:
a first transmission-information setting table in which the error and the device-related information are associated with each other,
wherein the endoscope data transmission unit transmits the device-related information associated with the generated error as the second endoscope-running data with reference to the first transmission-information setting table in a case where the error is generated.

3. The processor device for an endoscope according to claim 1, further comprising:
a second transmission-information setting table in which the error, the device-related information, and a transmission volume level regarding a volume of the second endoscope-running data to be transmitted are associated with one another,
wherein the endoscope data transmission unit transmits the device-related information, which is associated with the error and the transmission volume level, as the second endoscope-running data with reference to the second transmission-information setting table in a case where the error is generated.

4. The processor device for an endoscope according to claim 3,
wherein the transmission volume level is determined according to a communication situation of the specific network.

5. The processor device for an endoscope according to claim 4,
wherein the volume of the device-related information to be transmitted is increased as a transmission speed of the specific network is higher.

6. The processor device for an endoscope according to claim 3,
wherein the transmission volume level is determined by a user's setting.

7. The processor device for an endoscope according to claim 1, further comprising:
a transmission volume level-changing unit that changes a transmission volume level regarding a volume of the second endoscope-running data to be transmitted,
wherein the endoscope data transmission unit transmits the second endoscope-running data that is based on a transmission volume level changed by the transmission volume level-changing unit.

8. The processor device for an endoscope according to claim 1,
wherein the first endoscope-running data includes at least identification information of the endoscope, identification info nation of the light source device, or identification information of the processor body.

9. The processor device for an endoscope according to claim 1,
wherein the first timing and the second timing are the same timing or different timings.

10. An endoscope data collection server connected to a processor device for an endoscope through a specific network, the server comprising:
a processor, configured to:
receive first endoscope-running data transmitted from the processor device for the endoscope through the specific network at a first timing; and
receive second endoscope-running data, which is transmitted from the processor device for the endoscope and of which a volume is larger than a volume of the first endoscope-running data, through the specific network at a second timing, a timing when an error is generated, to notify that at least one of the endoscope, a light source device, or a processor body in an endoscope system is not operating normally according to a monitored result of the at least one of the endoscope, the light source device, or the processor body, wherein
the error comprises an abnormality indicating the monitored result of at least one of the endoscope, the light source device, or the processor body is out of range, and
the second endoscope-running data is device-related information related to operation information, working information, or processing information of the endoscope, the light source device, or the processor body.

* * * * *